United States Patent
Thompson

(12) 
(10) Patent No.: US 8,517,911 B1
(45) Date of Patent: Aug. 27, 2013

(54) SOUND DELIVERY SYSTEM FOR VIBRO-ACOUSTIC TREATMENT

(76) Inventor: Jeffrey D. Thompson, Encinitas, CA (US)

(*) Notice: Subject to any disclaimer, the term of this patent is extended or adjusted under 35 U.S.C. 154(b) by 1800 days.

(21) Appl. No.: 10/893,077

(22) Filed: Jul. 17, 2004

(51) Int. Cl.
*A61M 21/00* (2006.01)

(52) U.S. Cl.
USPC .............................. 600/27; 601/47

(58) Field of Classification Search
USPC .............. 84/217; 181/129, 163, 164, 207, 181/141, 144; 600/26, 27; 601/46, 47, 148; 248/638; 5/613; 381/64, 113, 150; 128/899
See application file for complete search history.

(56) References Cited

U.S. PATENT DOCUMENTS

| | | | |
|---|---|---|---|
| 5,065,555 A * | 11/1991 | Kobori et al. | ................. 52/167.7 |
| 5,442,710 A | 8/1995 | Komatsu | |
| 5,553,148 A | 9/1996 | Werle | |
| 5,807,287 A | 9/1998 | Cheng | |
| 5,951,500 A | 9/1999 | Cutler | |
| 6,053,880 A | 4/2000 | Sleichter, III | |
| 6,104,820 A | 8/2000 | Soza | |
| 6,369,312 B1 | 4/2002 | Komatsu | |
| 6,409,655 B1 | 6/2002 | Wilson et al. | |
| 6,544,165 B1 * | 4/2003 | McNew | ........................... 600/27 |
| 6,682,494 B1 | 1/2004 | Sleichter, III et al. | |
| 6,702,767 B1 | 3/2004 | Douglas et al. | |
| 7,418,108 B2 * | 8/2008 | Oser | .............................. 381/401 |

FOREIGN PATENT DOCUMENTS

JP          09271502 A   * 10/1997

OTHER PUBLICATIONS

"Psycho-Sensory Integration Sonic Induction System: Sound Therapy Table", Jan. 30, 1997, http://www.inner-net.com/bmr/bmrpg2e.htm.*

* cited by examiner

*Primary Examiner* — Charles A Marmor, II
*Assistant Examiner* — Carrie R Dorna

(57) ABSTRACT

Sound delivery system (10) stimulates the two hemispheres of the brain separately by delivering different vibro-acoustic vibrations to the left and right sides of a person's body. Split resonator (30) includes left resonator member (32L) with attached left transducer (23) and right resonator member (32R) with attached right transducer (24). Left and right resonator members are spaced apart to prevent vibrations being transmitted between resonator members.

4 Claims, 1 Drawing Sheet

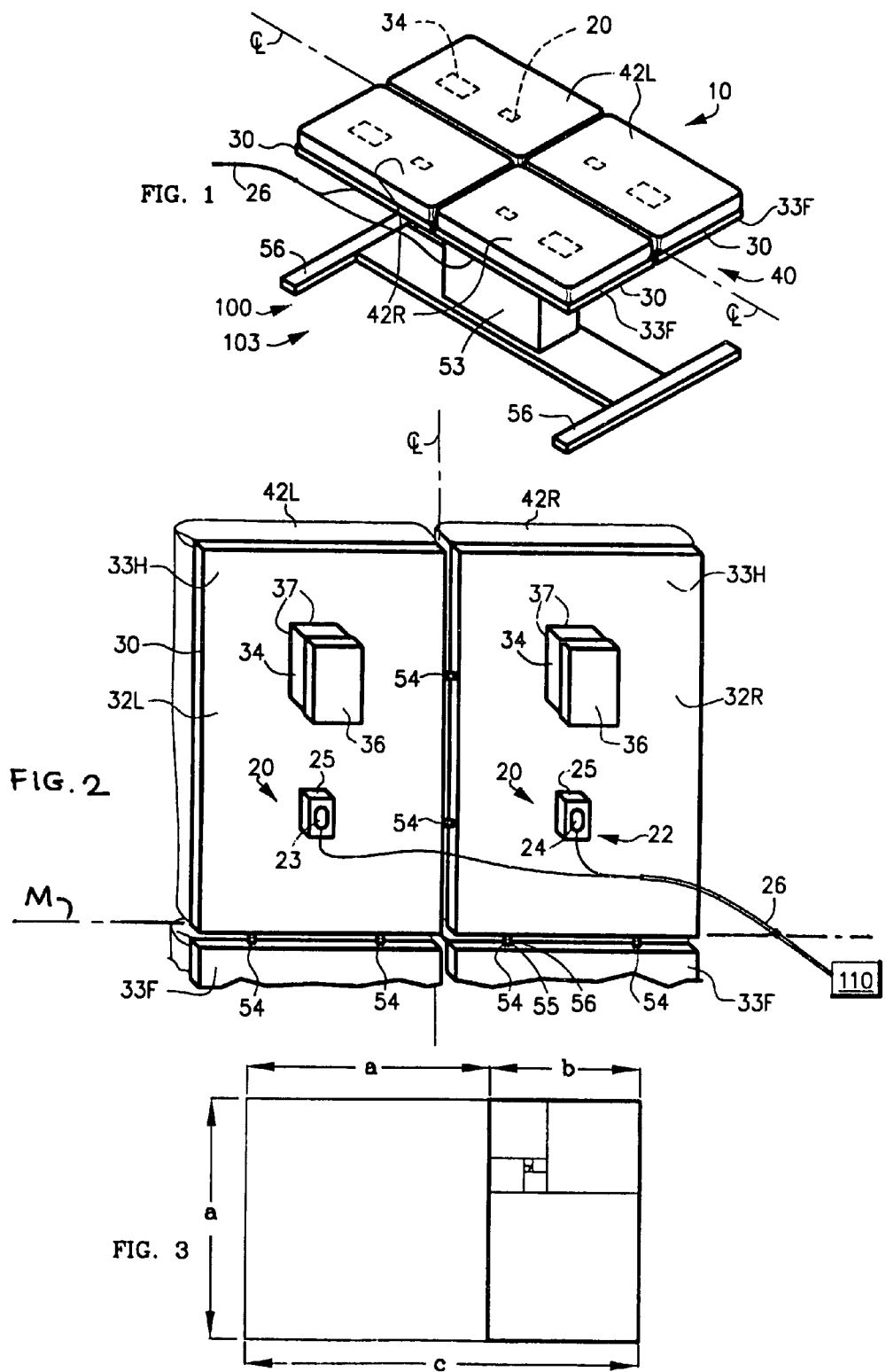

SOUND DELIVERY SYSTEM FOR VIBRO-ACOUSTIC TREATMENT

FIELD OF THE INVENTION

This invention relates to body supports for vibro-acoustic treatment, and more particularly to a body support with an integrated sound delivery system for stimulating each side of a person's body with different acoustic vibrations.

BACKGROUND OF THE INVENTION

Various means have been used to relax and soothe a person using vibrations in the acoustic range (generally 20 to 20,000 Hertz). For example, calming music is frequently delivered via conventional speakers or, headphones. Herein, vibration of the air or of a solid medium in the frequency range of 20 to 20,000 Hz will be generally called "sound vibration" or acoustic vibration." Vibration in that frequency range that is exclusively of the air and perceived by the ears will be called "audible vibration" or "audible sound."

Sometimes the delivery of calming music is combined with a pleasant visual display, as with a visor or helmet that includes both headphones and a device for displaying images to the eyes, for example colored lights that change in accord with changes in the music delivered by the headphones.

For example, Douglas et al. disclose in U.S. Pat. No. 6,702,767 an elaborate multi-sensory stimulation booth capable of presenting a person with colored lights or images, music or other sounds, aromas, and cool or warm breezes. The system is stated as producing either relaxation or entertainment, and is asserted as providing unusual perceptions, such as a feeling of floating.

Music or sound may be combined with a massage-like effect. The patents of Soza (U.S. Pat. No. 6,104,820) and Komatsu (U.S. Pat. No. 6,369,312), for example, disclose body relaxation systems that combine music with vibrations delivered to other parts of the body. In the case of Soza, music delivered to the ears by headphones is emphatically augmented by "massage" of muscle groups. The same electrical signals that are converted to sound by the headphones are also applied directly to the skin by electrodes. Komatsu discloses a chair in which music is played by speakers close to the ears, while transducers in the back and seat of the chair massage portions of the body with lower frequency vibrations (16 to 150 Hertz) that are related to the heard music in some manner, such as duration.

Conventional systems that combine vibration of parts of the body with audible sounds delivered to the ears by headphones or speakers have several shortcomings. Most obviously, headphones or helmets can interfere with relaxation and only deliver a small amount of vibro-acoustic energy. Speakers, even if built into a chair such that they are close to a person's head, by their nature put sound into the ambient air. The audible sound may be bothersome to other nearby persons or interfere with the relaxation therapy of other persons.

Less obviously, certain types of music or sounds are thought of as being relaxing, but individual persons have individual responses to any music or sounds. For example, some people are soothed by sounds of thunder and pouring rain; others find such sounds very distressing. Any audible sounds delivered by means of a person's hearing are filtered through that person's culture, experiences, and aesthetic taste, among many factors.

Speakers or headphones can transmit very little energy into a person for two reasons. Firstly, strong sounds damage the ears, so there is a strict upper limit to the amplitude of audible vibrations that can be delivered safely. Secondly, speakers, including those of headphones, vibrate the ambient air to transmit sound energy in an expanding sphere of sound. Not much energy is actually received by any given spot on the human body. The ears perceive the sound because they are exquisitely sensitive to vibrations in the acoustic range. Only the very loudest audible sounds are perceived by the rest of the body, but such loud sounds are unsuitable for use therapeutically because they are ear-damaging.

Devices that directly vibrate portions of the body other than the ears deliver approximately 25 times the vibration energy to a body that speakers or headphones do, for a given input energy. Direct vibration of the body also allows greater energy to be imparted without risk of damage to the ears. However, direct vibration of the body, as taught by Soza or Komatsu, for example, is typically perceived as a simple "buzzing" sensation that is relaxing by its anesthetic effect on the muscles.

Researchers and therapists have believed for some time that sensory stimulation affects a person more quickly and deeply if the stimulation targets the halves of the brain separately. By simultaneously presenting each hemisphere of the brain with a therapy tailored to that hemisphere's functions and abilities, a well-designed therapy would proceed very quickly and with potential synergy between the hemispheres.

Attempts have been made to provide bi-lateral stimulation of the brain hemispheres by use of specialized headphones or visors. As discussed above, the amount of acoustic energy that can be transmitted by headphones is very limited. Another weakness of administering bi-lateral acoustic sound through headphones is that the sound travels to the brain via the acoustic nerve only. The sound is evaluated according to taste and experience, as discussed above, with certain sounds possibly having unintended significance due to positive or negative conditioning.

An attempt has been made (McNew, U.S. Pat. No. 6,544,165) to stimulate the halves of a person's body with vibrations from speakers attached in pairs to a body support. The speakers are shown attached to the bottom of a body support, with small holes to help the sound penetrate to the supported body. The speakers are surrounded by attenuating housings to prevent sound from being emitted into the ambient air.

This apparatus bypasses the problems of using the ears as the object of the sensory stimulation, but maintains the weakness of trying to stimulate the skin with audible sound instead of vibration transmitted by a solid medium.

Also, separation of the vibro-acoustic vibrations to separate sides of the body is not complete, even with "attenuating housings." Vibrations will be transmitted throughout the support, which is disclosed as being of wood or metal, among other materials. This mixing of the vibrations severely undercuts the aim of providing different stimulations to the two sides of the body and, hence, the brain.

There is a need for an apparatus that can stimulate the two sides of the human body with different and discrete vibrations in the acoustic frequency range.

There is a need for comfortable article's of furniture of various types for delivering bi-lateral acoustic stimulation to the brain and brainstem in order to promote relaxation, stress relief, or sleep.

SUMMARY OF THE INVENTION

The present invention is a sound delivery system for delivering sound vibrations in a manner profoundly more effective for therapy than conventional headphones or vibrating massagers.

The sound delivery system generally includes a resonator split along a longitudinal centerline, including a left resonator member for transmitting vibro-acoustic vibration to the left half of a person's body in contact with the left resonator member, and a similar right resonator member. The split resonator is optionally attached to a furniture frame that raises the sound delivery system to a desired height above the floor and may include an adjustable central pedestal or four legs.

Each left or right resonator member is attached to one of a pair of transducers, namely a left transducer and a right transducer, that are connected to a source of input signal. Typically, each left or right resonator member receives a different input signal, which is converted to vibro-acoustic vibration that is transmitted to the respective side of the body.

The left and right resonator members are not in vibrational communication.

Other features and many attendant advantages of the invention will become more apparent upon a reading of the following detailed description together with the drawings wherein like reference numerals refer to like parts throughout.

BRIEF DESCRIPTION OF THE DRAWINGS

FIG. 1 is a perspective top, three-quarter view of the sound delivery system of the present invention, configured as a treatment table.

FIG. 2 is a perspective view from below, partly cut away, of the sound delivery system of FIG. 1, removed from the frame whereby the system was configured as a treatment table.

FIG. 3 is a geometrical representation of the golden ratio rectangle relationship.

DETAILED DESCRIPTION OF THE INVENTION

FIG. 1 is a perspective top, three-quarter view of the sound delivery system 10 of the present invention, configured as integral to an article of furniture 100, such as treatment table 103. Table 103 includes frame 53, floor contact means 56, and an upper portion comprising sound delivery system 10 of the present invention.

Sound delivery system 10 is for delivering sound vibrations separately to the left and right sides of a human body in contact with sound delivery system 10, such as the body of a patient lying upon table 103, and generally includes paired vibration means 20 and a split resonator 30 for transmitting vibrations received from vibration means 20 to the two sides of the body.

For the purpose of this description, it is assumed that the person taking treatment will lie supine on table 103. Reference to the "left" or "right" sides of the person's body will be relative to that position. All parts of the invention herein designated "left" (L) or "right" (R) refer to parts that are supporting or delivering sound vibration to either the left or right sides of the person's body. Centerline C lies between the left and right halves of sound delivery system 10 and would roughly correspond to the spine of a person lying supine upon table 103.

Sound delivery system 10 of FIG. 1 is illustrated as divided into quadrants. Transverse midline M divides sound delivery system into a "head" portion that delivers sound vibration to a person's body generally above the waist and a "foot" portion that delivers sound vibration to a person's body generally below the waist. The division of sound delivery system 10 along transverse midline M is optional and included only for convenience of manufacture or use.

Sound delivery system 10 preferably includes body support means 40 for contacting and supporting a reposed or reclining body. Body support means 40 includes left pad(s) 42L for supporting the left side of a supported body and right pad(s) 42R for supporting the right side of a supported body.

Although in FIG. 1 two left pads 42L are shown, 42L could alternatively comprise a single pad 42L running the length of the left side of sound delivery system 10, or three or more pads 42L; the same is true for the two right pads 42R.

FIG. 2 is a perspective view from below, partly cut away, of sound delivery system 10 of FIG. 1, shown removed from frame 53.

Split resonator 30 includes a left resonator member 32L for transmitting vibrations to the left side of the body and a right resonator member 32R for transmitting vibrations to the right side of the body. It is a requirement of the invention that split resonator 30 be divided along longitudinal centerline C, at least such that vibro-acoustic vibrations cannot pass from one side of centerline C to the other side.

In the figures, left and right resonator members 32L,32R are depicted as being each further divided into a head portion 33H and a foot portion 33F, although this is not a required feature of the invention.

Resonator members 32 L,R are constructed of a material that is strong, resilient, and that conducts vibro-acoustic vibration well. Typical materials used are 0.125" thick hardwood and 0.060" thick steel sheet.

In the exemplary view of FIG. 2, vibration means 20 consists of pairs 22 of transducers, such as left transducer 23 attached to left resonator member 32L and right transducer 24 attached to right resonator member 32R. Pairs 22 of transducers are attached to resonator 30, such as mounting each transducer 23,24 on a mount block 25 by suitable means, such as screws, and attaching mount block 25 to the appropriate left or right resonator member 32 L,R by suitable means, such as wood glue. Several pairs 22 of transducers may be employed, but at least one pair 22 is required for sound delivery system 10 to function. Pairs 22 of transducers are connected to a source 110 of input signal. Source 110 provides suitable electronic signals via input cable 26 to pair 22.

Source 110 typically provides a different signal to left transducer 23 than is provided to right transducer 24. Each transducer 23,24 converts the input signal into a vibration in the "acoustic" range of 20 to 20,000 Hz, typically in the lower end of the range, such as 20 to 500 Hz. The vibration created by each transducer 23,24 is transmitted through mount block 25 and into the associated resonator member 32L,R, respectively. The vibration spreads throughout resonator member 32 L,R. The vibration stimulates the skin of the side of the body in contact with each resonator member 32 L,R.

As is well known, the vibrations applied to the left side of the body are received by the right half of the brain stem and upper brain, and the reverse is also true. There are various therapeutic reasons for stimulating the two halves of the brain simultaneously with different frequencies of vibration. For example, when the frequencies received by the halves of the brain differ by only about 18%, the left and right halves of the brain compare received frequencies and generate a "difference frequency," that is, a third frequency that is the difference between the frequencies of vibrations applied to the left and right sides of the body. This act of comparing and cooperation can have a beneficial effect upon the brain, helping the two halves of the brain become synchronized and operating at more equal strengths. More importantly, the brain waves can become "entrained" to that generated frequency, artificially inducing a desired state, such as relaxation or sleep.

Thus, the stress relief produced by vibrating the two sides of the body at two carefully-chosen frequencies is far more effective than the superficial relaxation caused by simply vibrating the entire body at a single frequency or a series of frequencies, such as frequencies derived from music.

When two different frequencies are presented in the form of audible, that is, air-borne, sound, the difference frequency is generated in the air itself by physical interaction of the compression waves in the air. This phenomenon is often noticed in the sound of two musical instruments played together but at frequencies a few Hz apart, or the sound of a twin engine airplane. The difference frequency is perceived as a throbbing whine that changes in pitch and amplitude as the sounds of the instruments or engines vary.

Some attempts to modify brainwaves have used a pair of loudspeakers for stimulating the two halves of the brain via the auditory nerves; but in this case, both ears actually hear all three tones, although the relative loudness of the tones will be different for the two ears. In this case, no synchronization of the two hemispheres of the brain is induced.

The present invention resolves the shortcomings of mixing of the frequencies between sides of the body (as in the patents of Komatsu and McNew) and generation of a difference frequency within the resonator 30 by complete vibro-acoustic isolation between left resonator member 32L and right resonator member 32R. The members 32L, 32R are spaced apart from each other, therefore there is a small gap along the longitudinal centerlines C of split resonator 30 and body support means 40.

In an alternative preferred embodiment of the invention, the centerline gap may be bridged, either for comfort or for structural stability, or both. The material bridging the gap must be non-conductive to vibrations in the acoustic range.

The centerline gap may be bridged for the comfort of the supported body by insertion of a strip of vibration-damping material between left pad 42L and right pad 42R, such as a non-slumping silicone gel (not shown). Left and right pads 42L,42R are composed of material that provides comfortable body support and that conducts vibro-acoustic vibration well, at least in the direction perpendicular to the horizontal plane defined by left and right pads 42L,42R.

The gap between head and foot resonator members 33H, 33F may be bridged in similar fashion if desired. Because the gap between head and foot members 33H,33F is optionally provided only for convenience of use or manufacture, it is not necessary to the function of the invention that the bridging material be of vibration-damping material.

In FIG. 2, left and right resonator members 32 L,R are shown connected for structural stability by vibration damping connecting means 54, such as stud 56 encased within a casing 55 made of vibration damping gel, inserted into matching holes in the edges of left resonator member 32L and right resonator member 32R. It is not required for the function of the invention that left and right resonator members 32 L,R be divided into head and foot members. All resonator members to the left of longitudinal centerline C receive a same left input signal from source 110 and all members to the right of centerline C receive a same right input signal, which is typically different from the left input signal, but may in some cases be identical.

Resonator members 32 L,R optionally include a pair of amplifying boxes 34 L,R. Each amplifying box 34 is constructed of four sides 37 and a bottom 36, which are attached together to form a hollow box, such as by screws or wood glue. The top, or open, side of the box is attached to the underside of a resonator member 32 L,R, such as by wood glue. If the dimensions of amplifying box are in proper relationship to the dimensions of resonator member 32 L,R, vibration of resonator member 32 L,R will cause amplifying box 34 to vibrate spontaneously at the same frequency, known as "sympathetic" vibration.

In the embodiment illustrated, each resonator member 32 L,R and 33 H,F is a rectangle of the type known as a "golden ratio rectangle." The general aspect of a golden ratio rectangle is illustrated in FIG. 3. The large rectangle has a width 'a' and a length 'c' that is the sum of 'a' plus 'b'. Large rectangle ac can be subdivided into a square having sides 'a' and a smaller rectangle ab. The ratio of 'a' over 'b' is about 1.618. The smaller rectangle ab can be similarly subdivided into a square and a rectangle with sides having a length ration of about 1.618. Thus, the golden ratio can be used to generate an infinite family of similar rectangles; each a golden ratio rectangle that is smaller than its predecessors.

Bottom 36 of amplifying box 34 is a golden rectangle from the family of rectangles derived from the dimensions of resonator members 32 L,R and 33 H,F. By use of these related dimensions, sympathetic vibration of amplifying box 34 is ensured.

Transducers 23,24; mount blocks 25; and amplifying boxes 34 are all depicted as attached to the under surface of resonator members 32,33 for clarity. This attachment is convenient and has the advantage that transducers 23,24 may be easily replaced, if necessary. The sound delivery system 10 of the present invention would also function if some or all of these components were attached to the upper surfaces of resonator members 32,33 or within recesses let into resonator members 32,33. This method of manufacture does not allow for such simple repair, but provides a sleeker appearance.

Sound delivery system 10 is illustrated herein as integrated into an article of furniture 100, such as a treatment table 103. Table 103 includes a frame 53, including floor contact means 56. Resonator members 32 L,R and 33 H,F are attached to frame 53. Frame 53 is typically constructed of wood or steel. If the design and materials of frame 53 are such that vibro-acoustic vibrations can be communicated from one resonator member 32 or 33 to another resonator member 32 or 33 on the opposite side of centerline C, resonator members 32 or 33 are attached to frame 53 by suitable vibration damping attachment means 54. Attachment means 54 may be the combination of a stud 56 and a gel casing 55, as discussed above, or other suitable means.

Sound delivery system 10 may also be adapted as other articles of furniture 100, such as a couch or chair contoured to fit the body comfortably. To integrate sound delivery system 10 into a contoured chair, it may not be optimal to divide resonator 30 into four congruent golden rectangles, as shown in the case of table 103. Resonator 30 may be split into two elongate left and right resonator members 32 L,R; each member 32 having the aspect of a golden rectangle. Sound delivery system 10 would also function properly if resonator 30 is split into any number of pairs of resonator members 32 L,R, each pair of which has the aspect of a golden rectangle.

Alternatively, sound delivery system 10 may be configured as a foldable or rollable pallet that may be placed on a floor or bed. In such an embodiment, resonator members 32 and 33 would typically be connected together by soft straps or hook-and-loop fasteners. Sound delivery system 10 would be folded into quarters for storage, or if resonator members 32, 33 be made of flexible material, such as thin steel sheets, sound delivery system 10 could be rolled for storage.

Although particular embodiments of the invention have been illustrated and described, various changes may be made in the form, composition, construction, and arrangement of the parts herein without sacrificing any of its advantages. Therefore, it is to be understood that all matter herein is to be interpreted as illustrative and not in any limiting sense, and it is intended to cover in the appended claims such modifications as come within the true spirit and scope of the invention.

I claim:

1. A sound delivery system for delivering sound vibrations separately to the left and right sides of a human body, including:
   one or more pairs of left and right transducers for converting electronic signals to vibrations, said left and right transducers of each pair being capable of delivering a signal independent of each other;
   a left resonator member having said left transducer of each transducer pair vibrationally coupled thereto;
   a right resonator member having said right transducer of each transducer pair vibrationally coupled thereto; and
   an input signal source capable of delivering a signal at a first set of one or more frequencies to said left transducer of each transducer pair and a signal at a second set of one or more frequencies, different from said first set, to said right transducer of each transducer pair;
   each resonator member dimensioned as a golden ratio rectangle, and further comprising: a hollow amplifying box enclosing each transducer and attached to the underside of the resonator member, wherein each amplifying box and the resonator member are constructed of material of substantially identical composition and thickness, and wherein the face of each amplifying box parallel to the surface of said resonator member is dimensioned as a golden ratio rectangle having a length and width that is derived from the length and width of the resonator member for creating sympathetic amplification of vibrations transmitted through said resonator from each respective transducer;
   wherein said left resonator member and said right resonator member are not in vibrational communication with each other, because of a mid-longitudinal split therebetween;
   and wherein said left and right resonator members vibrate at the frequencies produced by the transducers attached respectively thereto.

2. The sound delivery system of claim 1, wherein said left and right resonator members are bridged by a vibration damping material.

3. The sound delivery system of claim 1, said mid-longitudinal split further comprising:
   a left body support attached to the upper surface of said left resonator member for supporting the left side of a human body; and
   a right body support attached to the upper surface of said right resonator member for supporting the right side of a human body;
   wherein vibrations are transmitted from said left and right transducers through said left and right body supports.

4. The sound delivery system of claim 1 wherein said frequencies delivered to said left transducers and said frequencies delivered to said right transducers are minimally different such that a person perceiving said frequencies could detect a difference frequency.

* * * * *